US008206975B2

(12) United States Patent
Bao et al.

(10) Patent No.: US 8,206,975 B2
(45) Date of Patent: Jun. 26, 2012

(54) METHOD AND DEVICE FOR REGULATING FLUID FLOW IN MICROFLUIDIC DEVICES

(75) Inventors: Xiaoyan Robert Bao, Pasadena, CA (US); Stephen R. Quake, Stanford, CA (US); Melvin I. Simon, La Jolla, CA (US)

(73) Assignee: California Institute of Technology, Pasadena, CA (US)

( * ) Notice: Subject to any disclaimer, the term of this patent is extended or adjusted under 35 U.S.C. 154(b) by 1185 days.

(21) Appl. No.: 11/588,852

(22) Filed: Oct. 27, 2006

(65) Prior Publication Data

US 2007/0134807 A1   Jun. 14, 2007

Related U.S. Application Data

(60) Provisional application No. 60/731,068, filed on Oct. 28, 2005.

(51) Int. Cl.
*C12M 1/34* (2006.01)
*C12M 3/00* (2006.01)

(52) U.S. Cl. ............... 435/288.5; 435/293.1; 435/288.4; 435/287.3; 436/177; 137/803; 137/806; 137/841

(58) Field of Classification Search ............... 435/288.5, 435/288.4, 293.1, 287.3; 436/177; 137/803, 137/806, 841
See application file for complete search history.

(56) References Cited

U.S. PATENT DOCUMENTS

| | | | |
|---|---|---|---|
| 5,942,443 A * | 8/1999 | Parce et al. ............... | 506/39 |
| 6,637,463 B1 * | 10/2003 | Lei et al. ............... | 137/803 |
| 6,793,753 B2 | 9/2004 | Unger et al. ............... | 156/155 |
| 6,899,137 B2 | 5/2005 | Unger et al. ............... | 137/833 |
| 6,929,030 B2 | 8/2005 | Unger et al. ............... | 137/833 |
| 7,040,338 B2 | 5/2006 | Unger et al. ............... | 137/15.19 |
| 2001/0029983 A1 * | 10/2001 | Unger et al. ............... | 137/597 |

OTHER PUBLICATIONS

Anderson and Van Den Berg, "Microfluidic devices for cellomics:a review," 2003, Sensors and Actuators B, 92, 315-325.
Chung, B.G., et al., "Human neural stem cell growth and differentiation in a gradient-generation microfluidic device," 2005, Lab on a Chip, 5, 401-406.
Elowitz, M.B., et al., "Stochastic Gene Expression in a Single Cell," 2002, Science, 297, 1183-1186.
Lahav, G., et al., "Dynamics of the p53-Mdm2 feedback loop in individual cells," 2004, Nature Genetics, 36, 147-150.
Lee, P.J., et al., "Microfuidic application-specific integrated device for monitoring direct cell-cell communication via gap junctions between individual cell pairs," 2005, Applied Physics Letters, 86, 223902.
Studer, V., et al., "Scanning Properties of a low-actuation pressure microvalve," 2004, Journal of Applied Physics, 95, 393-398.
Taylor, et al., Microfluidic 2005, Nature Methods, 2, 599-605.
Teruel, M.N., et al., "Parallel Single Cell Monitoring of Receptor Triggered Membrane Translocation of a Calcium Sensing Protein Module," 2002, Science, 295, 1910-1912.
Thorsen, et al., "Microfluidic Large-Scale Integration," Science, 298:58-584.
Unger, et al., "Monolithic Microfabricated Valves and Pumps by Multilayer Soft Lithography," 200, Science, 288:113-116.
Wheeler, et al., Microfluidic Device for Single Cell Analyis, Analytical Chemistry, 75, pp. 3581-3586 (2003).

(Continued)

*Primary Examiner* — William H Beisner
*Assistant Examiner* — Danielle Henkel
(74) *Attorney, Agent, or Firm* — Kilpatrick Townsend & Stockton LLP

(57) ABSTRACT

A method and a microfluidic device are provided to regulate fluid flow by equalization of channel pressures. The fluid flow is regulated by way of valve-actuated channel pressures.

16 Claims, 20 Drawing Sheets

OTHER PUBLICATIONS

Agirregabiria et al., "Fabrication of SU-8 multilayer microstructures based on successive CMOS compatible adhesive bonding and releasing steps," *Lab Chip* 5:545-552 (2005).

Rhee et al., "Patterned cell culture inside microfluidic devices," *Lab Chip* 5:102-107 (2005).

* cited by examiner

FIG. 4a
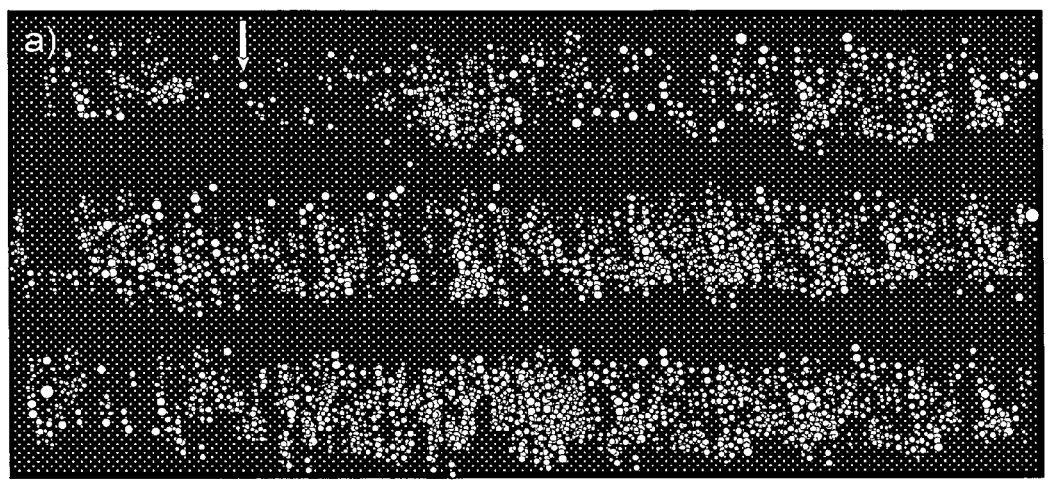
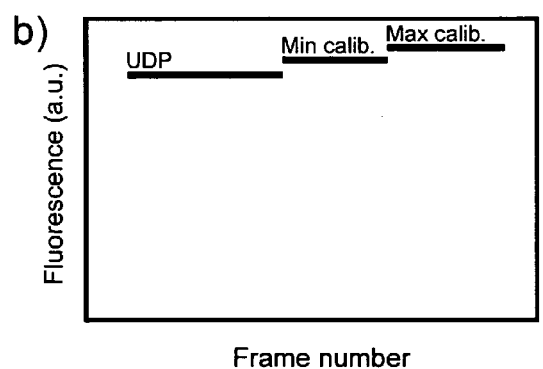
FIG. 4b
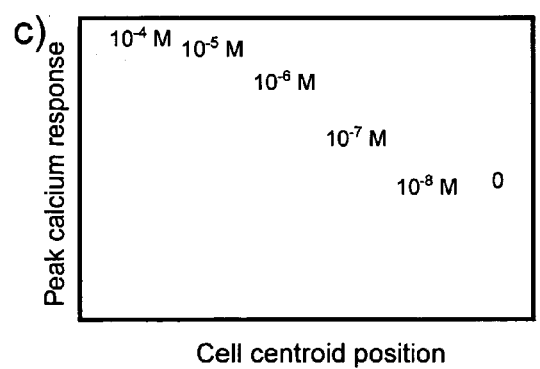
FIG. 4c

METHOD AND DEVICE FOR REGULATING FLUID FLOW IN MICROFLUIDIC DEVICES

CROSS REFERENCE TO RELATED APPLICATIONS

This application claims priority to U.S. Provisional Ser. No. 60/731,068 for "Microfluidic Platform for Performing Fluorescence Assays on Mammalian Cells" filed on Oct. 28, 2005, which is incorporated herein by reference in its entirety.

STATEMENT OF GOVERNMENT SUPPORT

The invention described herein was made in the performance of work under a grant from the National Institute of Health (NIH), Grant No. R01 HG002644. The U.S. government may have certain rights in the invention.

BACKGROUND

1. Field

The present disclosure relates to a method and device for regulating fluid flow in microfluidic devices. In particular, it relates to methods for providing cells to a microfluidic device wherein fluid regulation relies on the equalization of pressures and a microfluidic device for performing the same.

2. Description of Related Art

Automated systems to perform fluorescence experiments on cells have been around for a while. Molecular Devices' FLIPR and FlexStation systems, for instance, can perform hundreds of cellular calcium assays simultaneously. These, however, do not have single cell sensitivity. Assays on thousands of single cells can be performed, but with the same conditions stimulating all of them (Teruel and Meyer. 2002, *Science*, 295, 1910-1912). Conditions can also be varied in experiments, but this is currently possible only with either low throughput (Wheeler, et al., 2003, *Analytical Chemistry*, 75, 3581-3586) or with a solute gradient (Chung et al., 2005, *Lab on a Chip*, 5, 401-406). PDMS (poly-dimethylsiloxane) microfluidic devices have enabled inexpensive rapid prototyping of sophisticated microfluidic applications (Unger, et al., 200, *Science*, 288:113-116; Thorsen, et al., 2002, *Science*, 298:58-584). Several disclosures have been made relating to microfluidic devices, their fabrication and uses thereof (U.S. Pat. No. 6,793,753; U.S. Pat. No. 6,899,137; U.S. Pat. No. 6,929,030, U.S. Pat. No. 7,040,338). U.S. Pat. No. 7,040,338 is incorporated herein by reference in its entirety.

Observing cells singly rather than as an ensemble is important since cells often have digital, stochastic responses to external stimuli (Elowitz et al., 2002, *Science*, 297, 1183-1186; Lahav et al., 2004, *Nature Genetics*, 36, 147-150). The nature of these responses can be masked when populations of cells are observed as a whole. The ability to do different experiments on identically prepared cells is also important, since many variables that influence cellular responses are difficult to control from batch to batch, experiment to experiment.

The approach to the problem as described herein, is to seed cells into molded poly(dimethysiloxane) (PDMS) microchannels, and then manipulate the environment that the cells experience by switching the solutions that flow over them with pressure-actuated valves (Studert et al., 2004, *J. of Applied Physics*, 95, 393-398). In this way, several microchannels can be packed into one field of view on a microscope, so that several different experiments can be performed on cells which originate from a single batch and which have experienced essentially identical manipulations.

In order to make cellular experiments compatible with a valve-gated microfluidic network, the method and device disclosed herein provides a new way of seeding microfluidic devices with cells. Until now, all devices that need to use cells load them either one at a time from a dilute cell suspension (Wheeler, et al., 2003, *Analytical Chemistry*, 75, 3581-3586; Lee et al., 2005, *Applied Physics Letters*, 86, 223902), or in one pass with a concentrated pass (Andersson and van den Berg, 2003, Sensors and Actuators B, 92, 315-325; Taylor et al., 2005, *Nature Methods*, 2, 599-605). The former approach becomes impractical in situations where high throughput and large numbers of cells are required. The latter, on the other hand, can cause problems when microfluidic valves are used since some cells will inevitable be trapped in, and crushed by, those valves.

This problem with trapped or crushed cells is especially troublesome in experiments involving macrophages. Assays on macrophage cell lines are of particular interest, since they have rather large and complex signal transduction systems. Macrophages, however, are programmed to respond to signs of nearby cell death. Thus, in a microfluidic device, care must be taken to prevent killing cells upstream of the cells that are being experimented on. In addition, macrophages are inherently adherent, and there is a significant possibility of adhesion to most surfaces when they suspension is stagnant, so it is difficult to selectively remove macrophages after they have adhered to a surface.

The disclosure presented herein provides for a new method and device relating to a PDMS microfluidic device.

SUMMARY

A new method and apparatus are provided herein for providing a cell suspension to a microfluidic device wherein control of the cell suspension is regulated by means of equalizing pressures within a microfluidic device designed to perform said method.

A microfluidic device according to the present disclosure allows for the seeding of cells (e.g. mammalian cells) to a microfluidic device, and then allows for the surrounding channels of the device to be cleared of cells without the need to close valves when and where cells are present, and with fluid flowing throughout the cell seeding process. Multiple experiments can be performed in parallel in a said device. Using said device, allows, for example, for an entire dose-response series, with single cell resolution, in one data acquisition run.

According to a first embodiment of the present disclosure, a method of providing a microfluidic device with a cell suspension is disclosed, the method comprising: closing at least two valves positioned in the microfluidic device such that fluid flow is directed to at least one reaction area; providing a cell suspension through at least one inlet of the microfluidic device; providing the cell suspension to the at least one reaction area; opening the at least two valves; flushing all regions of the microfluidic device except the at least one reaction area with fluid by equalizing pressures in channels of the microfluidic device.

According to a second embodiment of the present disclosure, a microfluidic device for providing cells to a reaction area is provided, wherein the microfluidic device comprises: at least one inlet manifold, wherein said at least one inlet manifold branches into at least two channels, connecting to at least one reaction area; at least two valves, wherein a first valve of the at least two valves is positioned within a first channel of the at least two channels, and a second valve of the at least two valves is positioned within a second channel of the at least two channels, such that when the valves are opened, a bypass channel is formed; at least one control channel, and a source of cells.

According to a third embodiment of the present disclosure, a method for controlling placement of cells to a region of a reaction area within a microfluidic device is provided, the method comprising: forming at least one channel in a first direction in the reaction area by way of at least two control channels; wherein said at least two control channels are positioned underneath the reaction area; forming at least one channel in a second direction in the reaction area by way of at least two control channels, wherein said at least two control channels are positioned above the reaction area; closing at least two valves positioned in the microfluidic device such that fluid flow is directed to the reaction area; and providing a cell suspension through at least one inlet of the microfluidic device to the reaction area.

According to a fourth embodiment of the present disclosure, a method for controlling placement of cells to a region of a reaction area within a microfluidic device is provided, the method comprising: providing bovine serum albumin (BSA) to non reaction channels through which a cell suspension will flow; forming four reaction channels in a first direction in the reaction area; providing fibronectin to the four reaction channels in the first direction; deforming the four reaction channels in the first direction; forming four reaction channels in a second direction in the reaction area; providing BSA to the four reaction channels in the second direction; deforming the four reaction channels in the second direction; providing a cell suspension to the reaction area, and binding cells to regions of the reaction area covered with fibronectin.

According to a fifth embodiment of the present disclosure, a microfluidic device for providing cells to a region in a reaction area is provided, wherein the microfluidic device comprises: a reaction area; at least one control channel for forming at least two channels in a first direction within the reaction area; at least one control channel for forming at least two channels in a second direction within the reaction area; at least two valves; an inlet channel providing a cell suspension and a cell-free media to at least one channel in the first direction in the reaction area and at least one channel in the second direction in the reaction area; and at least one bypass channel.

According to a sixth embodiment of the present disclosure, a microfluidic device for providing one from the group of: a biological molecule, a small molecule and a chemical, to a particular region of a reaction area, wherein the microfluidic device comprises: a reaction area; at least one control channel in a first direction for forming at least two channels in said first direction within the reaction area; at least one control channel in a second direction for forming at least two channels in said second direction within the reaction area; at least one valve to actuate the at least one control channel in the first direction; at least one valve to actuate the control channel in the second direction; an inlet channel providing fluid flow to at least one channel in the first direction, and at least one bypass channel.

Additional embodiments of the present disclosure are described in the specification, figures and drawings.

BRIEF DESCRIPTION OF THE DRAWINGS

FIG. 3a shows cells being injected into the cross channels; FIG. 3b shows the cross channels mostly stagnant after opening of the bypass valves; FIG. 3c shows the channels surrounding the cross channels flushed with medium.

FIGS. 4a-c show calcium responses of RAW264.7 macrophages stimulated by different concentrations of UDP.

DETAILED DESCRIPTION

A microfluidic device for providing cells (e.g. any biological cells, mammalian cells, etc.) to be assayed, e.g. fluorescently labeled and visualized, is provided herein. Additionally, a microfluidic device according to the present disclosure can be utilized to perform microassays of biological molecules, small molecules and/or chemicals.

A microfluidic device encompasses a device wherein fluids are manipulated within structures whose smallest dimensions are on the order of microns or less. A microfluidic device allows for mixing, synthesizing, and/or imaging of microscale amounts of fluid, and is commonly made of polydimethylsiloxane.

Figure 1A:
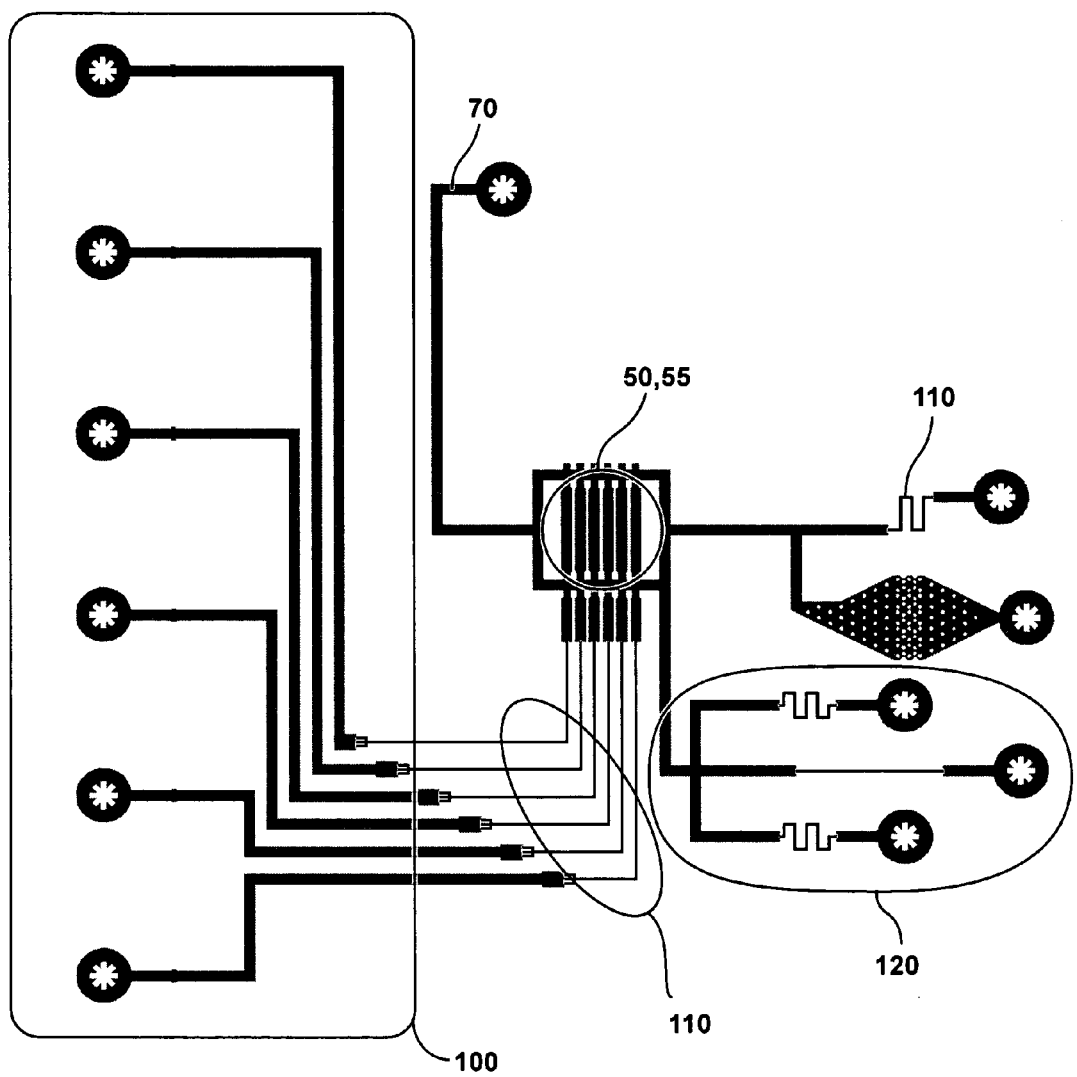
FIGS. 1a-d show a layout of a microfluidic device wherein fluid control is regulated by the equalization of pressures in the flow channels.
Figure 1B:
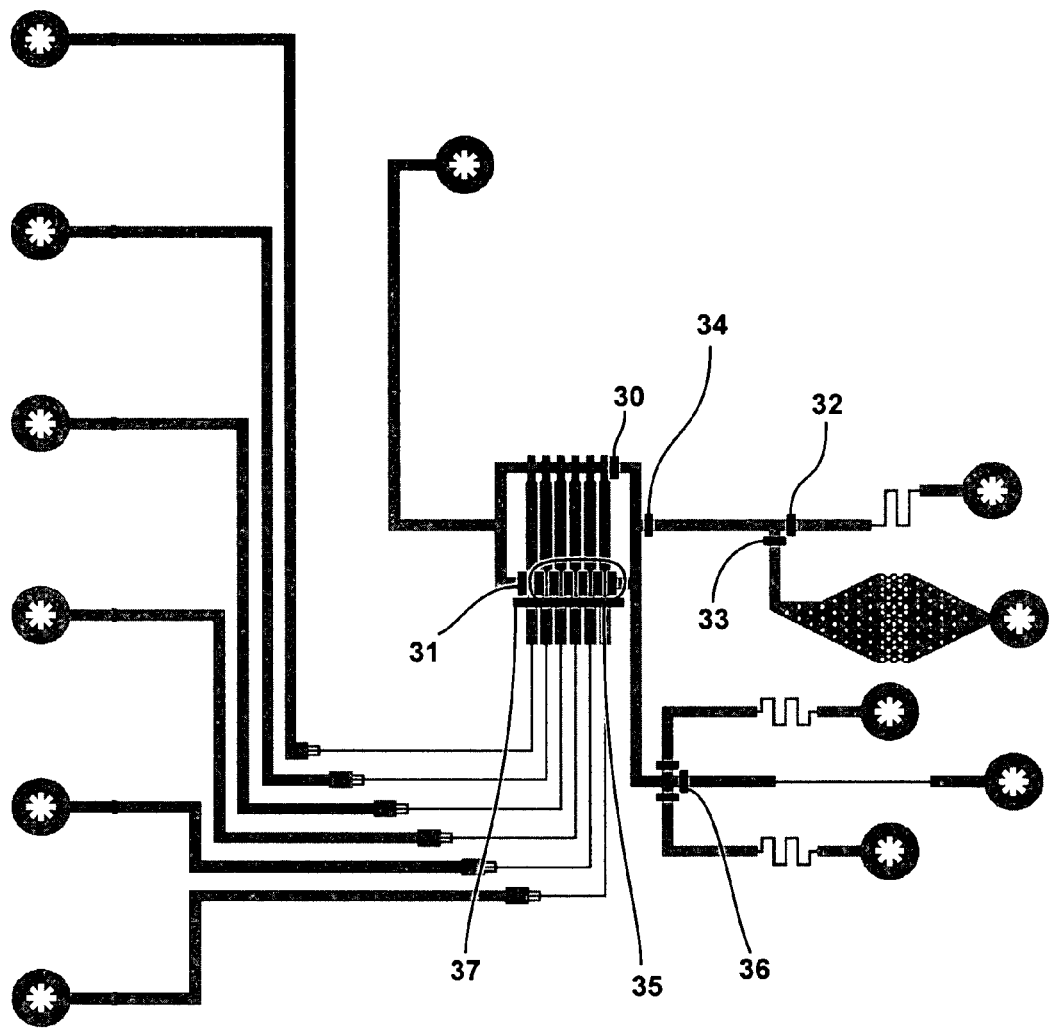
Figure 1C:
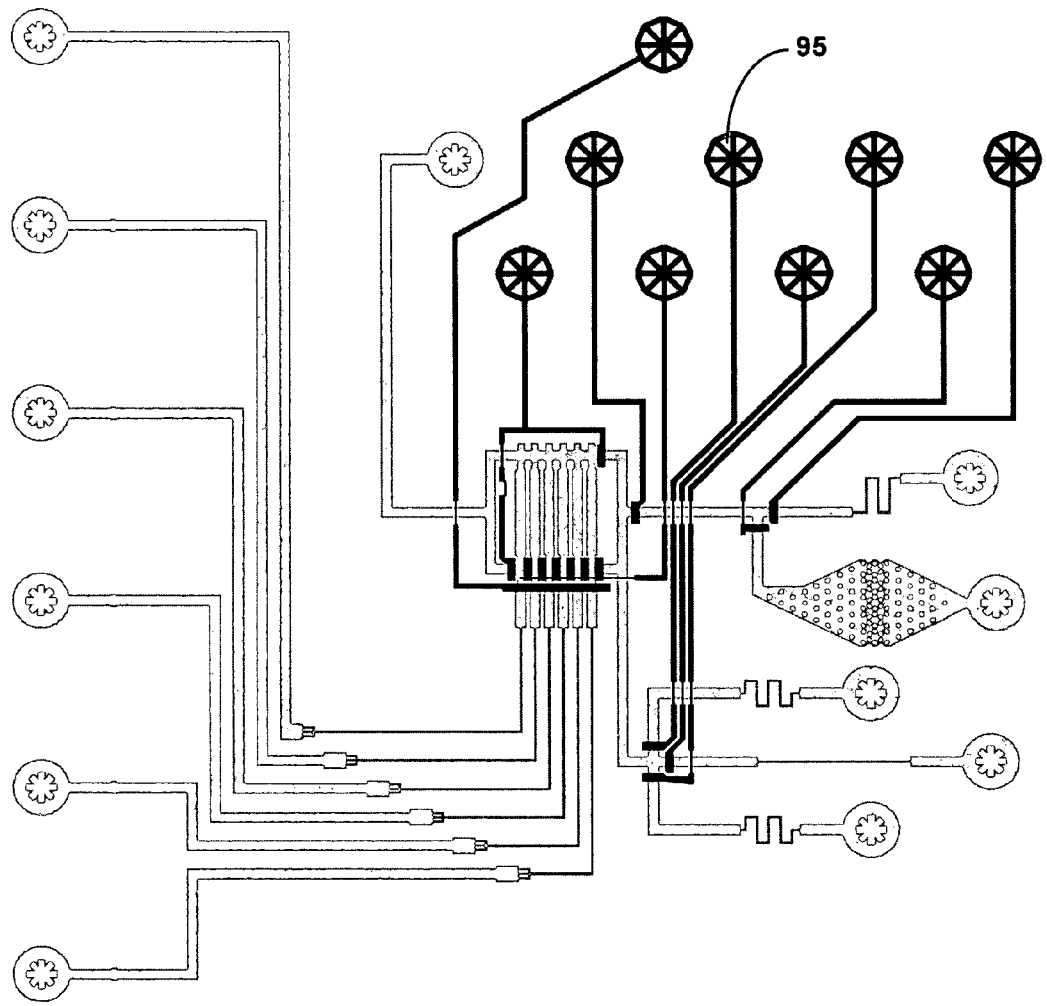

The microfluidic device, as shown in FIGS. 1a-c, details the following:

One inlet manifold (65) that branches into two channels (40), the two channels leading to and surrounding the cell reaction area (50)

A central cell reaction area (50), with stagnation cross channels (reaction wells) (55) and a bypass channel (45)

An inlet manifold (65) comprising a cell source (60) containing a cell strainer (70) to trap large cell clumps before they are distributed and a cell-free media reservoir (80)

A set of six inlet reagent channels (100) for feeding fluid directly to the reaction wells A second inlet manifold (120) for washing all reaction wells with various solutions Pressure-actuated valves (30-37) to switch and gate fluid flow Control channels (95) for actuating the valves A gas channel (90) positioned above the plane of the flow channels within the PDMS for providing carbon dioxide ($CO_2$) to the permeable PDMS in order to maintain the proper pH for cells in the reaction wells (55), and for providing oxygen for cellular metabolism.

It should be noted that valves can be "closed"/"actuated"/"pressurized", when the control line is pressurized so that the flow line is shut off, and "open", when the valve is not pressurized so that the flow line is open.

The term "cell suspension" as used herein, encompasses at least one cell in a fluid, and can also be referred to as "cells" or "fluid of cells". Further, a cell suspension can also include "a cell", for with the disclosed method and device, it is possible to perform assays with single cell detection.

The term "reaction channel" as used herein, is interchangeable with "reaction well", wherein both terms refer to the same channel in the reaction area of the microfluidic device.

This design allows us to seed RAW 264.7 macrophages and perform multiple experiments in parallel. The entire device is assembled atop a thin glass cover slip through which cells may be imaged; thermal control can be provided from the bottom as well, either with a temperature-controlled surface (such as a slide warmer) or a stream of warmed air as a heat source.

Design Principles

Flow constrictions. Many mammalian cells are sensitive to flow shear, and controlling that shear is important in maintaining the viability of cells. Typical channels that are large enough for mammalian cells to pass tend to be too large to provide meaningful fluidic resistance, so even with small height differences between inlet and outlet the gravity-induced flow tends to be too fast. Therefore, flow constrictors (110) in the flow channels are used to deliver liquid media (as opposed to cell suspensions) in order to better control those flow rates. Since the resistance of a channel scales as the third power of its height, resistances over a wide dynamic range can be controlled with straightforward fabrication steps.

Controlling and balancing flow rates in a set of parallel channels is essential in achieving consistent conditions across many experiments in one device. To ensure consistent flow rates in these parallel channels when their downstream connectivity makes them inequivalent, as in, for example, FIG. 1 when the reaction wells (55) are connected to individual flow channels (100), each channel must be driven with a flow current source rather than a fixed pressure. Here we can use the flow constrictors (110) to our advantage: just as a large voltage with a large resistance constitute an electronic current source, so a large driving pressure and a large flow resistance constitute a fluidic current source.

Lower height cross-unders. Typical control channel cross-unders known in the art (U.S. Pat. No. 7,040,338 which is incorporated herein by reference in its entirety) simply narrow the control channel when it crosses under a flow channel; the altered aspect ratio prevents flow channel closing when the control channel is actuated. While this scheme is adequate for other applications, it introduces problems with the devices presented here. Even though the flow channels are not completely closed, their floors are deformed, and the channel resistance does change. This change in resistance can give rise to flow imbalances. Furthermore, during cell loading, the floor deformations can induce cells to adhere to the floor or, in extreme cases, give rise to clogs in the flow channels. These problems were minimized by using cross-under control channels that are lower (10 µm in height) as well as thinner. The reduced height means that pressurized cross-under control channels are separated from flow channels by a thicker layer of PDMS, so any deformations that do occur are much smaller in amplitude.

Stagnant cross channel cell loading. A method of loading cells into a valved fluidic device without having cells trapped in the valves is further provided herein. Flow is stopped dynamically instead of statically, i.e. by equalizing pressures rather than closing off channels. Thus, after cells are injected (FIG. 2a), certain valves (30, 31) are opened which equalize pressures along the channels designed to contain the cells of interest, so that those channels would be protected from later media flushes without being specifically valved off. With this method, when the flushing occurs, the reaction channels (or reaction wells) (55) become stagnant as the pressure in the channels surrounding these central reaction channels are equalized, and the flushing fluid circulates, but does not flush the cells already provided to the reaction channels.

Barrier valve arrays. For applying this method to a complex multiple reaction device (FIG. 5a-c), channels needed to be addressed both columnwise and rowwise, but with as small a footprint as possible to maximize the density of experiments. To this end, a system whereby channels are defined, rather than gated, by valves and control channels is disclosed and shown herein. The cell reaction area (20) in this multiple reaction device (FIG. 5) is, when no valves are actuated, essentially a large open reaction chamber with a ceiling or upper layer held up by pillars. Control channels 4 and 5, when actuated form walls that push up from the floor of the reaction area and separate the reaction area into a set of horizontal flow channels. Likewise, control channel 6 can be actuated to form walls that drop down from the ceiling of the reaction area and separate it into a set of vertical flow channels (these are all in the flow channel plane). When both sets of channels are pressurized, they actuate around each other and form individual chambers (reaction wells) sealed off from one another. Control channel 8 can occlude all channels e-h, and control channel 2 can occlude all channels a-d.

Bypass channels. The multiple reaction device is designed to stimulate cells columnwise and rowwise at different times, and the transition between the two modes is important to consider. For instance, consider a situation where the central reaction area (20) is divided into columns that have been filled with different ligands from channels a-d (FIG. 5). If the flow is switched to rowwise, the ligands present in the chambers to the left will briefly wash over chambers to the right; this may contaminate future experimental results. However, ligands will also be present between the column inlet valves (control channel 2) and the top horizontal barrier valve (control channel 4); just opening up the isolation valves (control channel 1) and flushing with plain buffer will again allow ligands from the leftmost column inlet to wash over downstream columns, though in much lower quantities. In order to eliminate channel cross-contamination, bypass branches to flow channels were provided. These bypass channels are gated by control channel 3, around the central chamber, so that the entire access channel can be flushed clean with buffer before starting a flush of the central reaction area.

In addition to washing ligands, the bypass channels are useful in selectively coating parts of the central chamber with different proteins.

Device Design and Fabrication

The fabrication materials for and methods of fabrication of the microfluidic device of the present disclosure can be carried out as previously disclosed in the art (U.S. Pat. No. 7,040,338).

Masks. Mask designs were all in AutoCAD, with zero-width polylines defining regions. Devices boundaries give a 2 cm square size, with an extra 1 mm border around for cutting leeway and PDMS bonding. Four device patterns fit a 3" wafer. To help in the device alignment phase, some top layer designs have a small symbol denoting the position of the pattern within the mask. Masks were sized so that they more than cover the window on the holder in the mask aligner. This is important to prevent formation a weakly bonded fringe in the SU8 molds, and also helps in aligning the mask to the holder. Masks are printed onto transparencies at 20000 dpi. The emulsion side down since the thickness of the transparency sometimes widens the features and causes traces to merge: having the emulsion face down means that it is pressed right up against the photoresist during exposure, thereby limiting the defocus.

Molds. Molds were made on 3" silicon wafer. Control layer wafers went through a two-step SU8 process, with the lower height cross-under features (typically 10 µm) fabricated first and then followed by the normal height features (typically 30 µm). Ventilation layers were made with one layer of SU8, typically 40 µm. Flow layer wafers were first patterned with the flow constriction features in SU8 (5 µm), hard baked to 150 deg C. for 5 min, and washed with acetone and isopropanol to remove development reside. Flow channels were then defined in AZ50XT and rounded by baking at 150 deg C. for 5 min, resulting in channel peaks heights of about 54 µm.

Device construction, two molds. All molds were first exposed to trimethyl-chlorosilane (TMCS) vapors for at least 5 min. Sylgard 184 (Dow Corning) was mixed in two different ratios: 28 g base to 4 g cure (7:1), and 20 g base to 1 g cure (20:1). The 7:1 was poured onto the flow layer mold, degassed by vacuum, and baked for 13 min. It was also spun onto 24 mm×30 mm No. 1 glass cover slips at 4000 rpm and then baked for 14 min. The 20:1 was spun onto the control layer mold at 1400 rpm and baked for 14 min. After baking, the molded flow layer was diced and aligned to the control layer wafer, and subsequently bonded for 20 min. The combined chips were cut out of the control layer, lifted off the control layer mold, and had access ports punched with catheter hole punch tools (Technical Innovations). These were then pressed against the 7:1 silicone layers atop the cover slips and then bonded for 4 hours to overnight. The cover slip dimensions were intentionally chosen to leave two flanges of glass by which the device may be clamped to a holder. All bake and bonding steps were in a convection oven at 80 deg C.

Device construction, three layers. Because of the density requirements involved in packing multiple experiments into a single field-of-view on a standard microscope, the contact between the thick layer and the thin layer in a device was often too weak to pull the thin layer off its mold. Prior processing of the thick layer (e.g. another cycle of bonding for additional layers) exacerbated this problem. In these cases, the bottom layer had to be transferred off its mold and onto the glass substrate separately, in an approach similar to one used for fabricating complex multilayer SU-8 microstructures (Agirregabiria et al., 2005, *Lab on a Chip*, 5, 545-552). The upper layers could be bonded to this bottom layer afterwards.

Molds were exposed to TMCS vapors for at least 5 min. Sylgard was first mixed in two ratios: 28 g base to 4 g cure (7:1), and 25 g base to 1.2 g cure (20:1). 7:1 Sylgard was poured onto the vent layer (also the push-down layer for the alternative design) mold and spun onto glass cover slips at 4000 rpm. 20:1 Sylgard was spun onto the flow layer at 800 rpm and the control layer at 1300 rpm. Another 0.4 g cure was mixed into the 20:1 PDMS to yield 15:1, which was poured onto a plain silicon wafer. The glass-cover slips and vent and flow layer molds were cured for 15 min. The control layer mold was cured for 17 min, and the plain layer was cured for 32 min. The plain layer was diced into four pieces, about 1" in size each, and these pieces were pressed against the control layer features. This was baked for 20 min to bond, then peeled off carefully so that the control layer peeled off its mold. The control layers were then punched and pressed against the glass cover slips, and baked for another 20 min. Afterwards, the plain PDMS layer was peeled off the cover slip carefully, transferring the control layer onto the cover slip. Meanwhile, the vent layer was aligned against the flow layer and baked for 20 min; this was then punched, and aligned to the control layers atop the cover slips. These fully assembled devices were finally baked overnight to complete the bonding. While the flow layer in these devices were weaker, typically proof up to only 10 psi, the control layers were as robust, proof up to at least 30 psi.

Device Operation

Solutions. Most solutions follow the protocols published by the Alliance for Cell Signaling (AfCS; www.signalinggateway.org). Briefly, cell culture medium was Dulbecco's modification of Eagle's medium (DMEM), supplemented with 10% fetal bovine serum, 20 mM HEPES, and 2 mM L-glutamine (AfCS protocol #PS00000510). Thereafter, cell simulation solutions were all made up into Hank's balanced salt solution, supplemented with 25 mM HEPES, 2 mM probenecid, and 0.5% bovine serum albumin (HBP; AfCS protocol #PS00000589).

Device preparation. The control layer channels are deadend filled with DuPont Krytox 103 lubricant pressurized to 25 psi. Valves can typically be actuated with 15 psi pressure; but were usually operated at 10 psi more than their minimal actuation pressure. Valve pressures are controlled with electronically driven solenoid valves (Precision Dynamics and/or Clippard) that can be switched either manually or by computer. The central cross-channel area is first primed with 1 mg/ml fibronectin to enhance cell adhesion. The cell suspension and cell media inlets are then primed with RAW growth medium (see AfCS protocols).

Figure 2A:
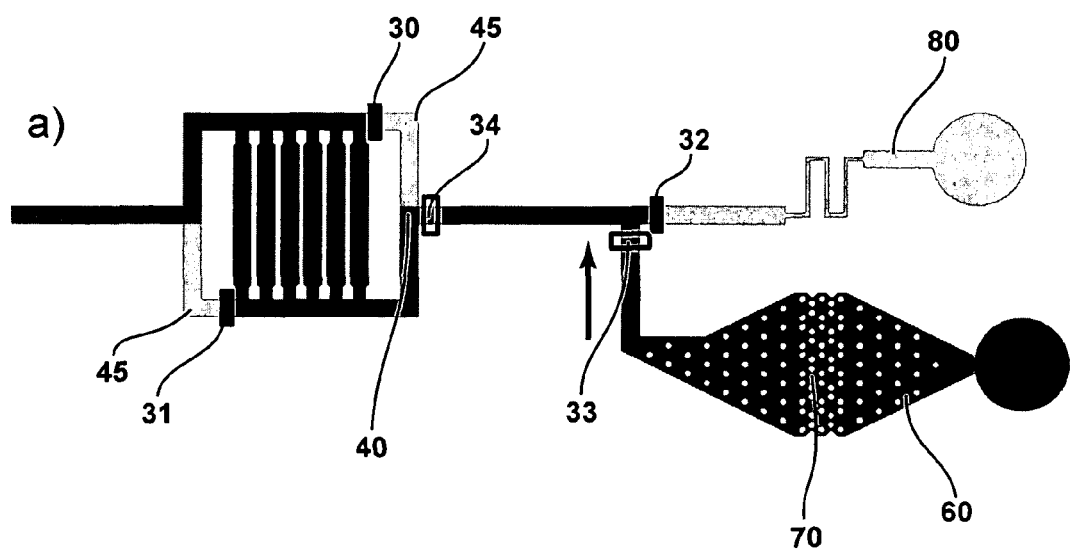
FIGS. 2a-d show schematics for loading cells into the microfluidic device without inducing cellular damage.

Cell seeding. RAW cells cultured in a plain polystyrene dish (60 mm diameter; not tissue culture treated; $\sim 10^6$-$10^7$ cells per dish) are removed by a combination of fluid shearing and treatment with 5 mM EDTA, centrifuged at 300 g for 5 min, aspirated, and resuspended in Dulbecco's phosphatebuffered saline (PBS), nominally free of divalent cations, supplemented with 10% fetal bovine serum. The suspension is centrifuged again, aspirated, and the cells are dissociated and suspended in 50-200 µl PBS with 5 mM EDTA. An equal volume of L-15 media, supplemented with 10 mM HEPES, 4 mM L-glutanine, 5 mM CaCl2, and 5 mM NaOH, is mixed into the cell suspension to saturate out the EDTA and provide cells with less stringent conditions. The cell suspension was immediately injected into the device from the cell source (60) (FIG. 2*a*), and excess cells are washed away by in a flushing step, whereby cells not reaching the reaction area are flushed through to the exhaust channel (70)(FIG. 1*a*) with a cell-free buffer media from the cell-free media source (80)(FIG. 2*a*).

The seeding protocol provided herein should work for any cell type for which a single cell suspension can be prepared with sufficient density, and for which a treatment for PDMS exists which enables adhesion. Since cell placement is determined by flow rather than some specific surface modification, selective attachment to the substrate is not a requirement. Further, the cell array can in principle be ready for use within minutes of cell injection, instead of having to wait for excess cells to either die off or detach from the surface (Rhee et al., 2005, *Lab on a Chip*, 5, 102-107).

Flow through the device is then shut, and cells are allowed to drift to the channel bottoms by gravity and to adhere. The bottom of the device is heated to 37 degrees Celsius to promote cell adhesion and recovery from the seeding process. After adhesion, the media channel is opened, driven by gravity, and cell-free media is allowed to flush slowly through the reaction area channels. When a third layer comprising gas channels is used to control the carbon dioxide content of the media, cells can be kept alive under these conditions for several days. They are typically kept in this condition from 30 minutes to 12 hours before stimulation. Devices are typically not sterilized before use; and bacterial contamination even with 12 hours of incubation has not been observed. Furthermore, the RAW macrophages did not show any morphological changes indicative of the presence of bacteria or bacterial products in the media.

Preparation for stimulation. While media is still flowing, one channel in the inlet manifold (100) was primed with a staining solution containing HBP supplemented with 4 µM fluo-3 AM and 0.02% pluronic F-127 (Molecular Probes). Once primed, the device was cooled to room temperature and the staining solution flowed over the cells, driven at 1 psi, for 4 minutes. Flow was then stopped and cells remained in the staining solution for another 26 minutes. Meanwhile, the two other manifold inlets (100) are primed with minimum calibration solution (HBP with 50 µM ionomycin, 5 µM thapsigargin, and 12.5 mM EGTA) and maximum calibration solution (HBP with 50 µM ionomycin, 5 µM thapsigargin, and 35 mM $CaCl_2$. The individual reaction wells (35) are primed with stimulation solutions, all made in HBP. While the flow is stopped, the supply tube for the staining solution inlet is switched with one containing HBP, and after the 30 minutes with staining solution that cells are washed with HBP, driven at 1 psi, for 5 minutes. The device is then warmed back to 37 degrees Celsius and incubated for at least 20 minutes before data acquisition.

Data acquisition. Data are taken on a Zeiss Axiovert 35 inverted microscope, with an Optronics Quantifire camera on the upper-left camera port. Illumination is provided by a 200 W mercury arc lamp (Oriel) shuttered electromechanically (Vincent Associates). A supply of warmed air is provided by an egg incubator (Lyon Electric) bolted sideways on the right side of the microscope; the air is streamed over the bottom of the device with an electric blower fan (Nidec). Full frame images (2048×2048, 12 bits per pixel) are taken with 0.5 second integration times, typically once every 5 seconds. Just after application of stimulants, however, the frame rate is increased to once every 2 seconds to improve time resolution, and during the calibration flushes the rate drops to once every 10 seconds to reduce photobleaching.

A typical acquisition run is as follows. First 24 dark frames for background subtraction are taken. Then another 12 illuminated frames are taken, once every 5 seconds. At this point valves (35) are closed, and valves (37) are opened. Opening valves (37) allow the solutions present in column inlet channels (100) to flow into the cell-containing reaction wells (55). Valves (35) prevent mixing of the different flow streams. In the experiment shown in FIG. 4, each column inlet channel (100) contains a different concentration of UDP which is a known calcium agonist for RAW264.7 macrophages, as indicated in FIG. 4c. Now as the cells are starting to respond to the solution present in the column inlet channels (100), 15 frames are then taken, once every 2 seconds, and then another 6 frames are taken at 5 second intervals before the channel inlets (15) are closed again. The cells stay in the stimulant solution for another 48 frames, with 5 second intervals. The isolation valves (35) are then opened, the first manifold (65) blocked by closing of valve (34), and one line of the second manifold (120) opened so that cells are flushed with the minimum calibration solution (cell free-media) for 4 minutes, with the acquisition rate slowing to once per 10 second after the first minute. Finally, the cells are flushed with the maximum calibration solution for 6.5 minutes, with the acquisition rate increasing to once per 5 seconds for the last 30 seconds. The minimum calibration solution is designed to deplete the cells' cytoplasm of free calcium ions, and the maximum calibration solution is designed to saturate the calcium-sensitive dye in that cytoplasm with calcium. Cellular fluorescence intensities during washes with these two solutions are used to convert those intensities during the rest of the experiment into measures of free cytoplasmic calcium concentrations.

Data analysis. Images are first background-subtracted with the average of the 24 background frames. The maximum-calibrated frames are then averaged and segmented to separate the brightly fluorescing cell features from the background pixels. The average intensity from these cell features are tracked over the entire acquisition run to determine intensity changes. Because each channel can carry a different ligand to the cells, an entire dose-response curve from one experiment on one batch of cells can be acquired (FIG. 4).

Example of a Multiple Reaction Microfluidic Device

A multiple reaction microfluidic device (FIG. 5) can improve data throughput for cells with lower tendencies to stick to passivated surfaces and each other. Columns in the reaction area of such a device can be stimulated with one set of ligands through channels a-d in a first direction as shown in FIG. 5, and then rows of chambers can be stimulated with another set of ligands through channels e-h in a second direction. This device in FIG. 5 can, in principle, perform sixteen different experiments simultaneously.

Preparation of the device and seeding of the cells is accomplished as follows (with reference to FIG. 5). First, with all valves closed, flow line j is dead-end filled with a 0.1% solution of fibronectin under pressure, and flow line i is likewise filled with a 35% solution of bovine serum albumen (BSA). After filling, these flow channels are pressurized to ~1 psi to drive fluid flow when valves are opened. Flow line x is filled with distilled water, and opening of valves 1, 3, 4, 5, 6, and 7 allows water to fill most of the rest of the flow channel, with the exception of the other inlet channels. Now, with valves 4, 5, and 6 closed, BSA is allowed to flush through and coat the bypass channels with the opening of valve 12. Closing valve 12 and opening valve 10 then flushes the same channels with fibronectin, though it is no longer able to bind the channel walls. Valve 6 is then opened, so that fibronectin fills the central chamber rowwise. The central reaction area has never contacted BSA, so the fibronectin coats its floor and ceiling. Flow is then switched back to BSA. When BSA fills the central reaction area, valves 4 and 5 are opened; the ceiling and floor of the reaction area at valves 4 and 5 have not seen any protein, so they are now coated with BSA. Now valve 6 can be closed so that cells can be provided to the reaction area.

After the protein coating, cell culture medium is injected via flow line j to fill the entire device with. A suspension of HEK293 cells, trypsinized and dissociated into single cells, is injected via flow line i. The cells reach the reaction area which is divided into segments coated with fibronectin and segments coated with BSA above valves 4 and 5. HEK cells cannot adhere to BSA-coated surfaces, so that after 20 minutes of adhesion at 37 degrees Celsius and in the absence of any flow, the cells in the valve areas can be washed out without affecting those cells that adhered to fibronectin-coated surface. In this way, cells outside the central reaction area, and cells inside the reaction area but in the areas above valves 4 and 5, can be removed after seeding. Cells cannot access the parts of the central reaction area below valve 6, since that valve is closed throughout the seeding process. The possible flow pattern of a 4 channel by 4 channel microfluidic device as described is shown in FIG. 6a-f. The resultant cell distribution of a 4 channel by 4 channel microfluidic device is shown in FIG. 7.

The problem with cell crushing during seeding is less serious here: the valve that stops flow of the cell suspension is number 12, which is never opened again. As valve 12 is about to close, it briefly acts as a filter, allowing fluid to pass through but trapping cells behind it. The residual fluid flow tends to dislodge cells from the downstream portion of the valve area, and cells crushed in the upstream portions never have their contents swept downstream after valve 12 is closed.

DESCRIPTION OF THE DRAWINGS

Figure 1D:
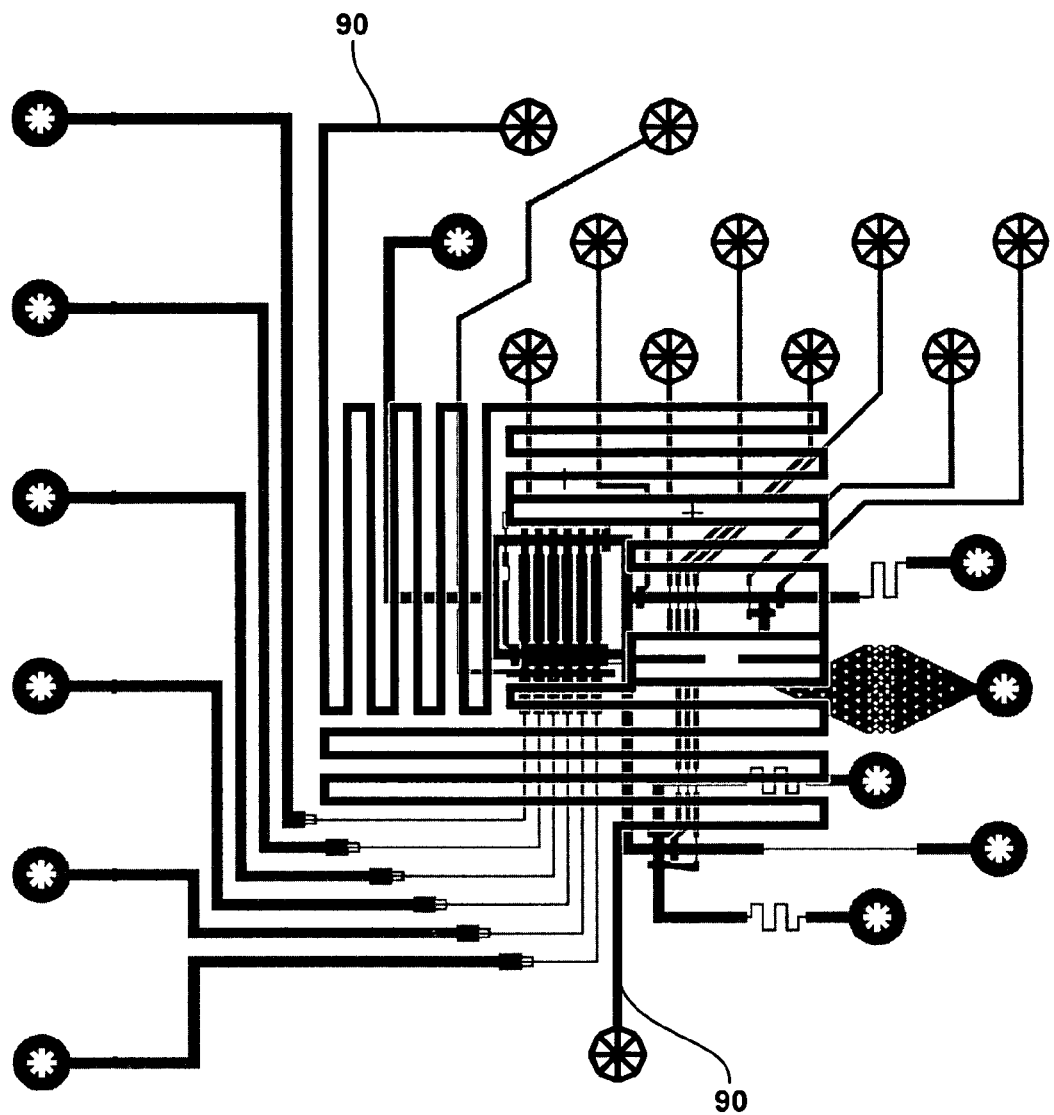

FIGS. 1a-d show a layout of the microfluidic device. FIG. 1a shows a layout of a flow layer, with the normal, rounded channels in gray and flow constrictions in black; FIG. 1b shows a layout of the flow layer, with black rectangles denoting the positions of pressure-controlled microfluidic valves as disclosed U.S. Pat. No. 7,040,338 (which is incorporated herein by reference in its entirety); FIG. 1c shows a device layout showing the full control channel in dark gray, with channels connecting inlet ports to their respective valves; FIG. 1d shows a device layout with the gas control channel design highlighted in black. Note that the gas channel never overlaps with the cell area—this is to prevent it from interfering with imaging.

Figure 2B:
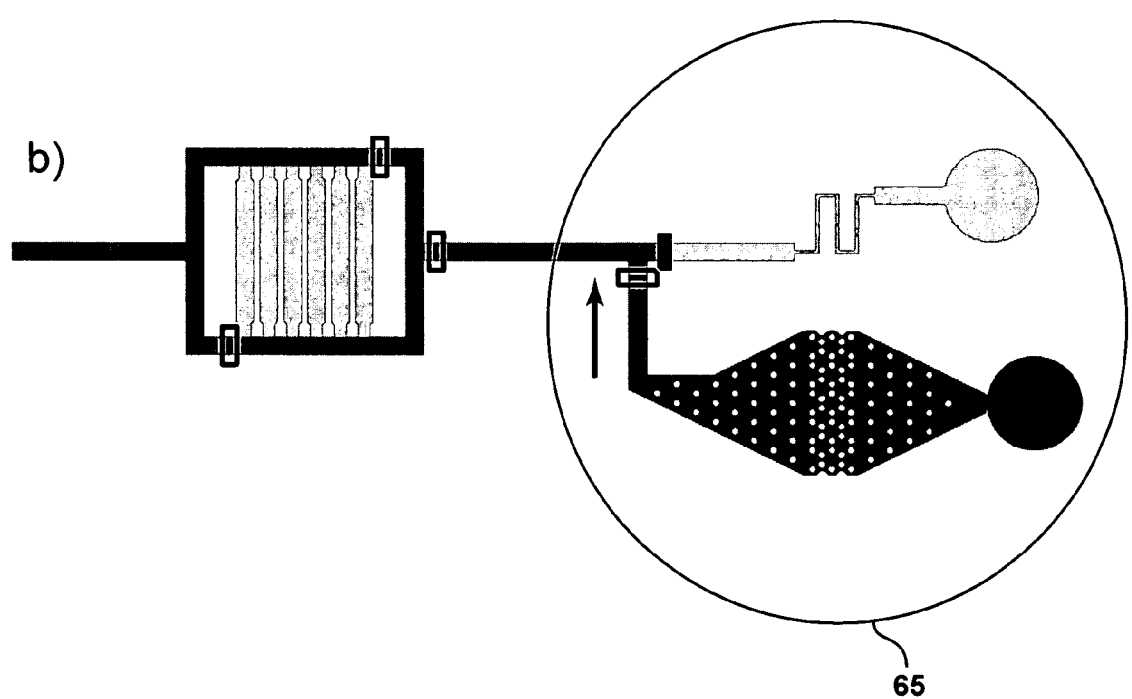
Figure 2C:
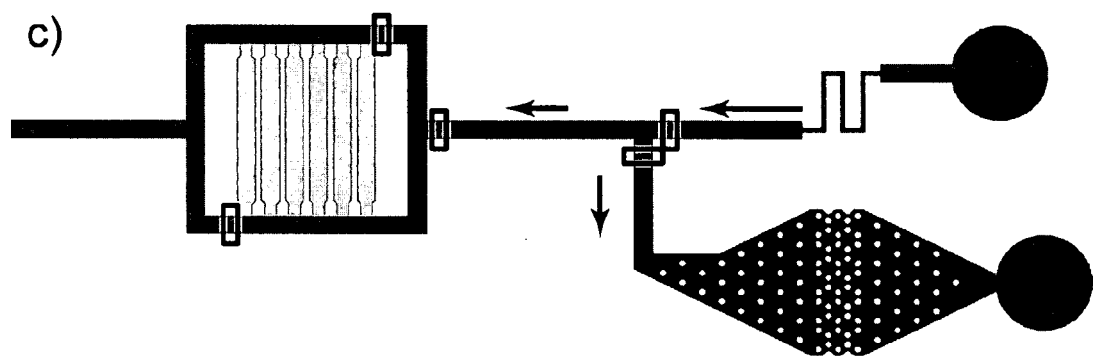
Figure 2D:
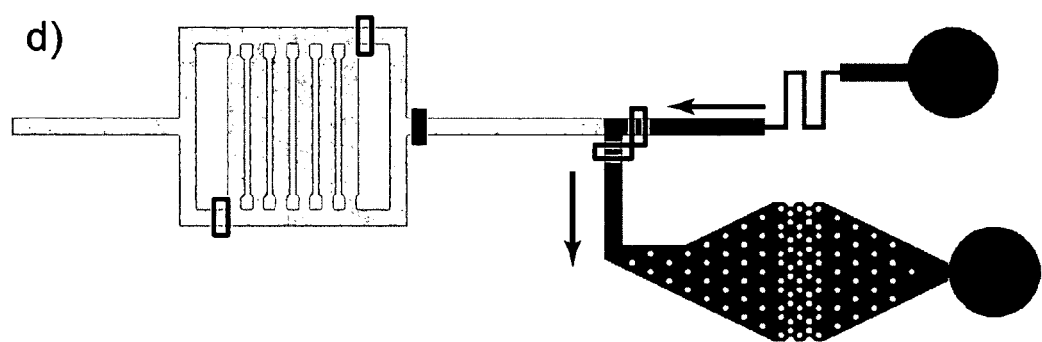

FIGS. 2a-d show schematics for loading cells into a device without inducing cellular damage. FIG. 2a shows injected cells go into the cross channels (55) because the bypass channels (45) are valved off. Because the flow is split several ways here, the flow is controlled with a small pneumatic pressure (~0.3 psi) to prevent cells from sticking near stagnation points when the flow is slowed down. FIG. 2b shows that opening the bypass channels by opening or releasing valves (30, 31) equalizes pressures across the cross channels (reaction wells), so they no longer carry flow. Once this happens the pneumatic pressure can be removed; flow driven by a small height difference between inlet and outlet (~5 cm). FIG. 2c shows the cell-free media inlet valve (32) when opened; the fluid flow is strong enough to reverse flow in the cell inlet, so the entire system, with the exception of the cross channels (reaction wells), is cleared of cells. There is still some residual flow in the cross channels (55), resulting from slight imbalances in the flow resistances between upper and lower branches of the flow channels (40), but most cells remain in the cross channels. FIG. 2d shows that after the cells have been cleared, the valve (34) which shuts off flow into the cross-channel reaction area can now be actuated, and the cell inlet can be further flushed with media. Note that, until this point, no valves have been closed.

Figure 3A:
FIGS. 3a-c show phase contrast images of the cell seeding process.
Figure 3B:
Figure 3C:
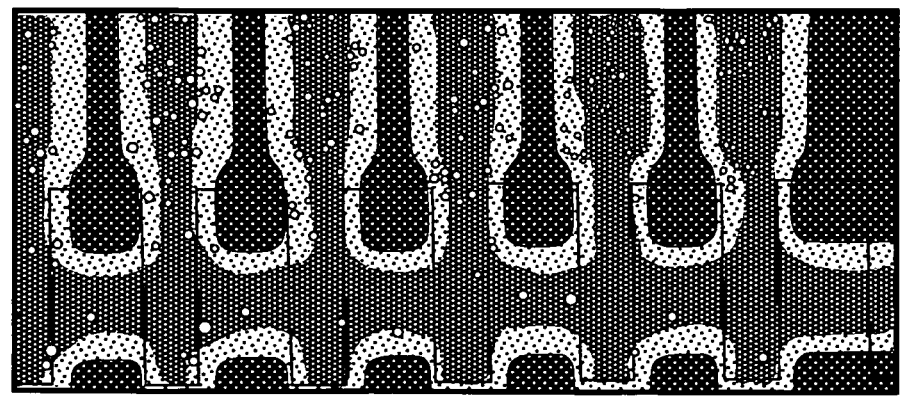

FIGS. 3a-c show phase contrast images of the cell seeding process: FIG. 3a shows cells being injected into the cross channels; FIG. 3b shows that with the bypass valves open (30, 31), the cross channels are mostly stagnant; FIG. 3c shows the cross channels when all the other channels have been flushed with medium FIGS. 4a-c show calcium responses of RAW264.7 macrophages stimulated by UDP. The experimental protocol is detailed in the Description section. FIG. 4a shows a fluorescence image taken after treatment with the maximum calibration solution, cropped to show only three cell channels; an entire data acquisition frame can encompass all six channels. FIG. 4b shows a time trace of fluorescence signal coming from the cell indicated by the white arrow in FIG. 4a. Here the frames were taken at 5 second intervals throughout the experiment. FIG. 4c shows a scatter plot of the peak calcium responses of cells, plotted against the vertical position of those cells to separate them according to the channel that they were in. The concentrations of UDP used in the channels are indicated. Peak calcium responses were rescaled to the minimum and maximum intensities, so that a value of 1 corresponds to the maximum calibration intensity and 0 corresponds to the minimum. Note that an entire dose response curve to UDP was acquired during this experiment.

Figure 5A:
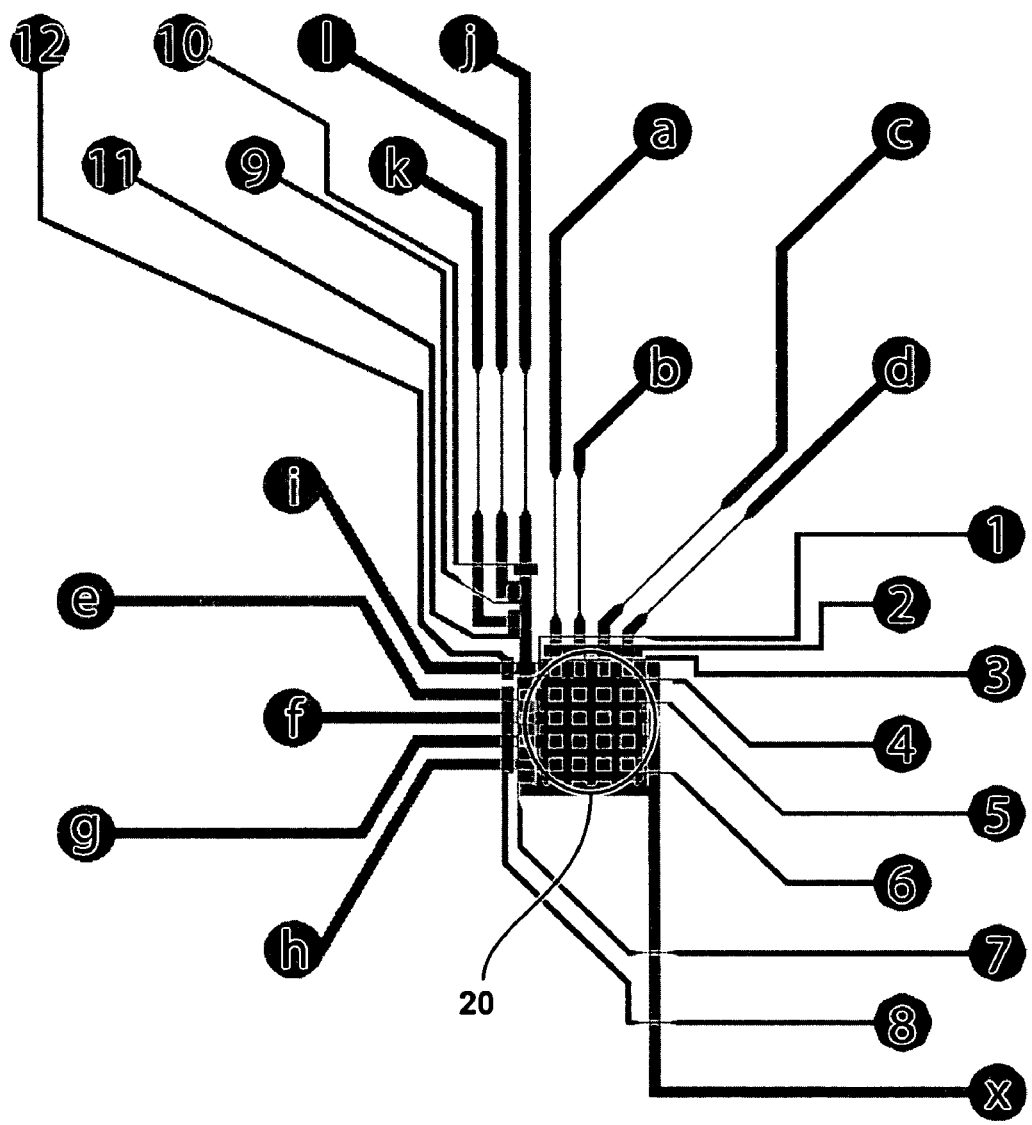
FIGS. 5a-c show a layout of a microfluidic device with sixteen experiment chambers which can be addressed either as four columns or four rows.
Figure 5B:
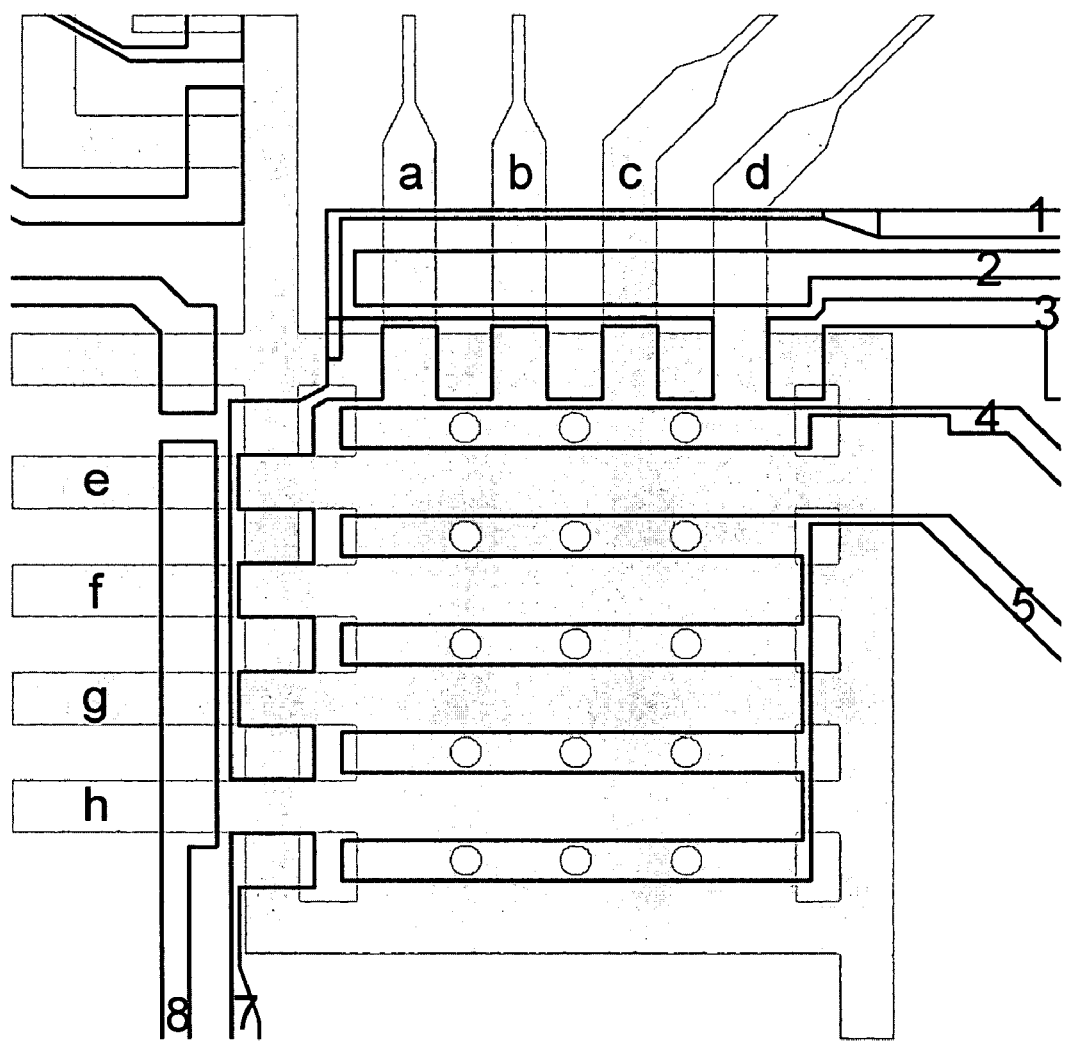
Figure 5C:
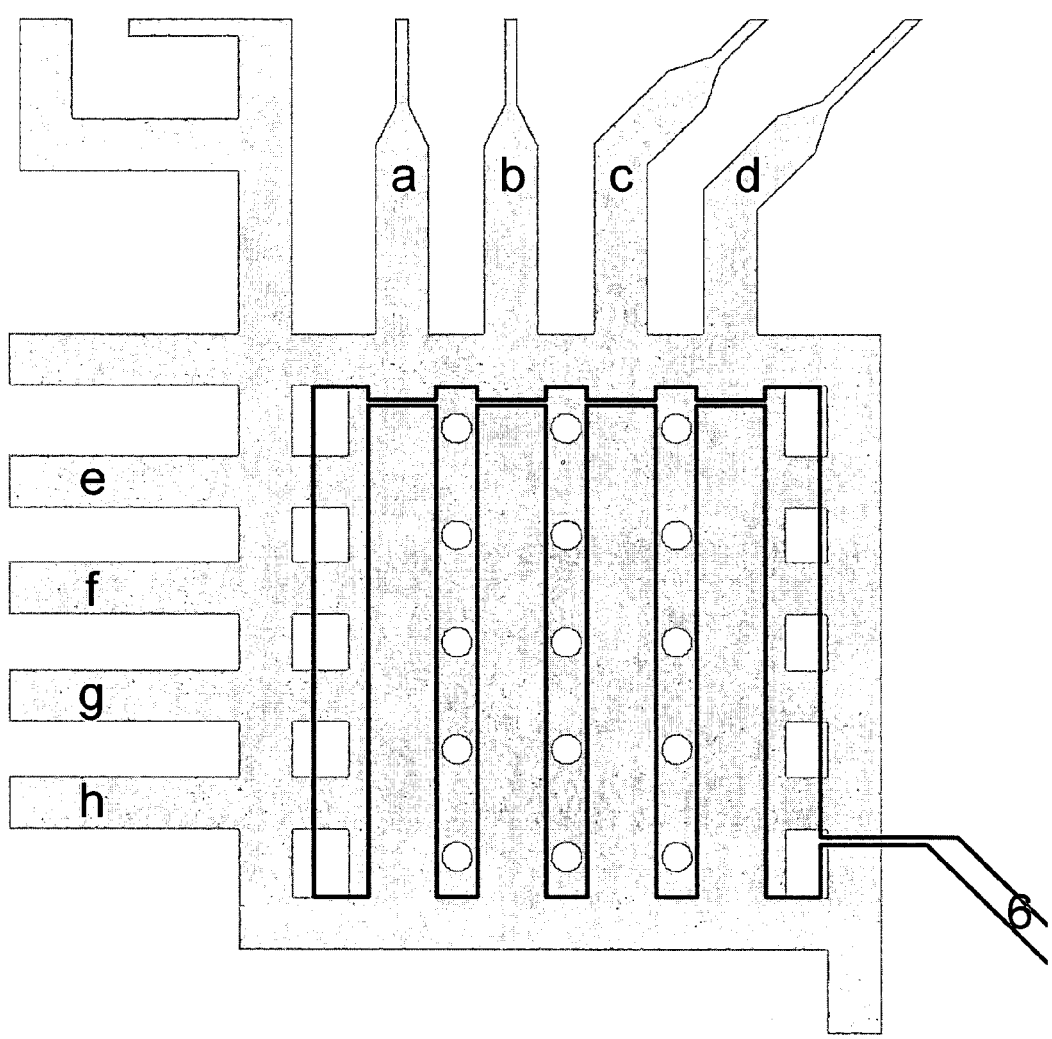

FIGS. 5a-c show a multiple experiment device, with sixteen experiment chambers which can be addressed either as four columns or four rows. FIG. 5a shows a general design layout with all flow channels (i-l), reaction channels (a-h) and control channels (1-12). FIG. 5b shows a close-up of the central reaction area, with the control channels underneath the flow channel plane outlined for clarity. FIG. 5c shows a close up of the central reaction area, with the control channels overlying the flow channel plane outlined for clarity.

Figure 6A:
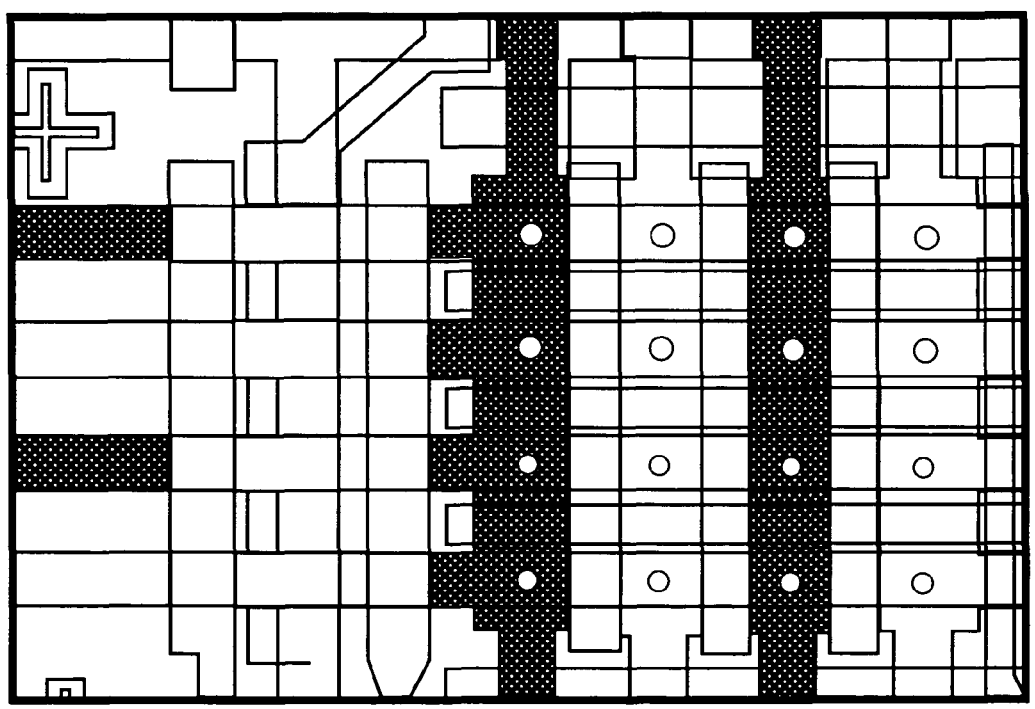
FIGS. 6a-f show a schematics of different flows achievable with the four row by four column microfluidic device.
Figure 6B:
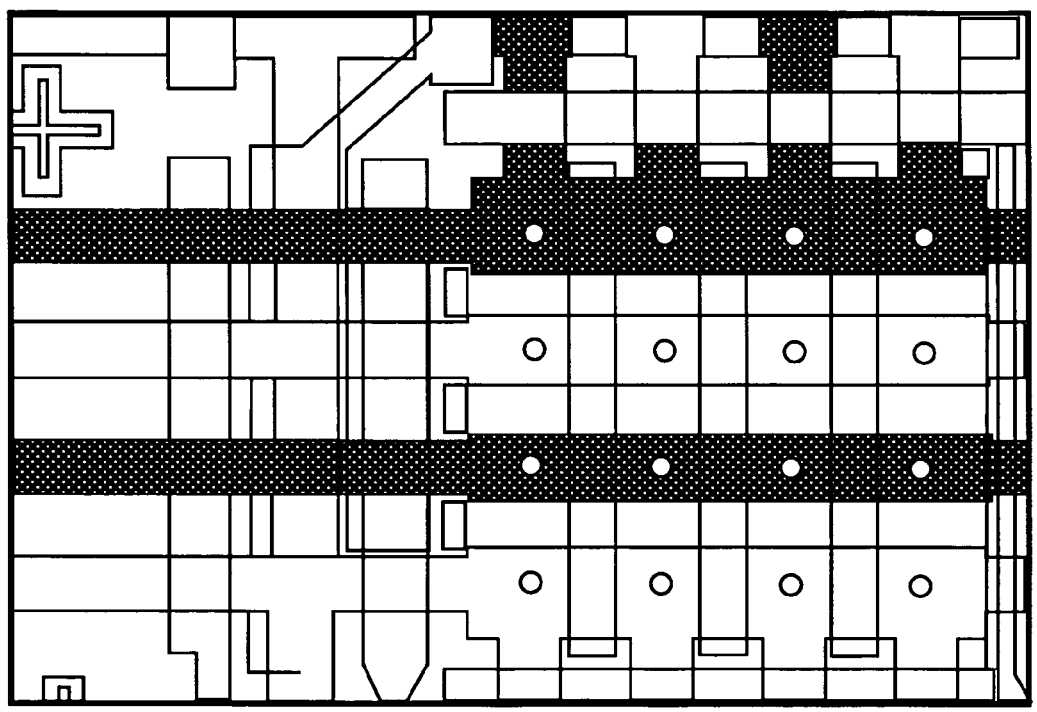
Figure 6C:
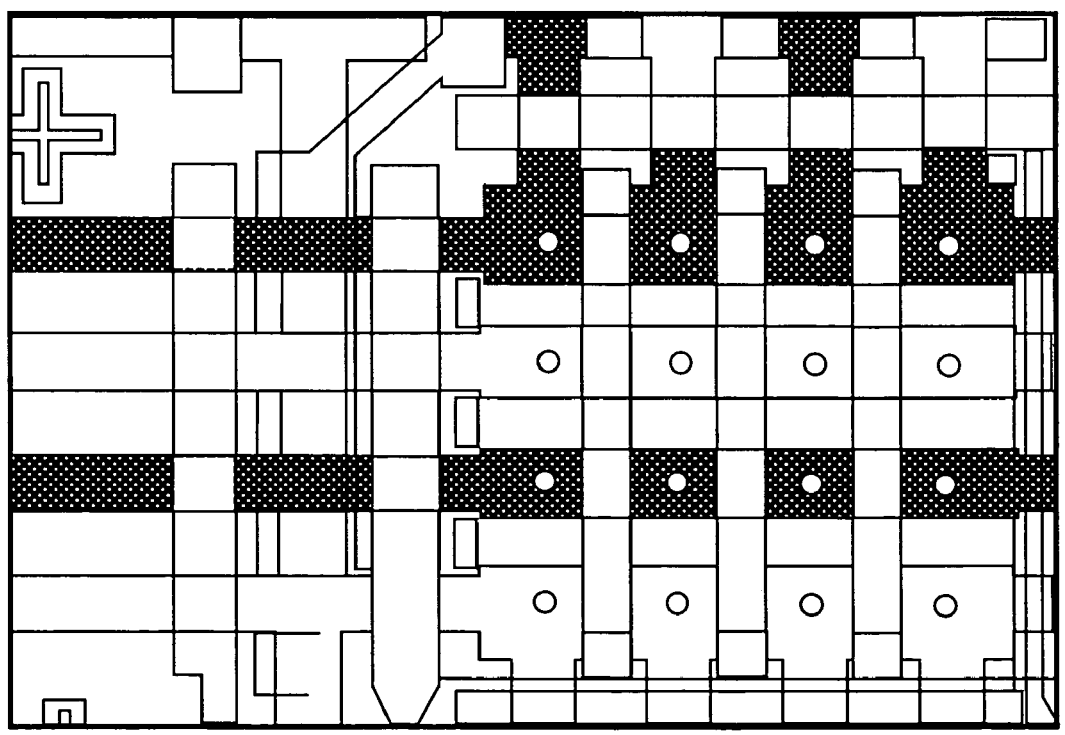
Figure 6D:
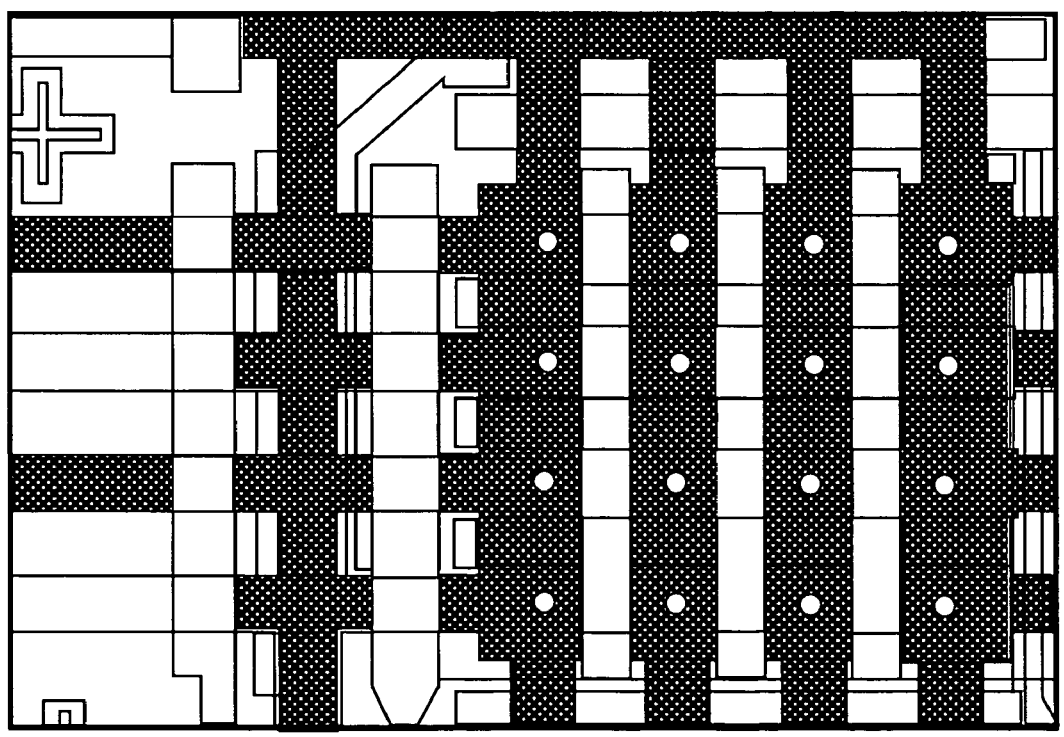
Figure 6E:
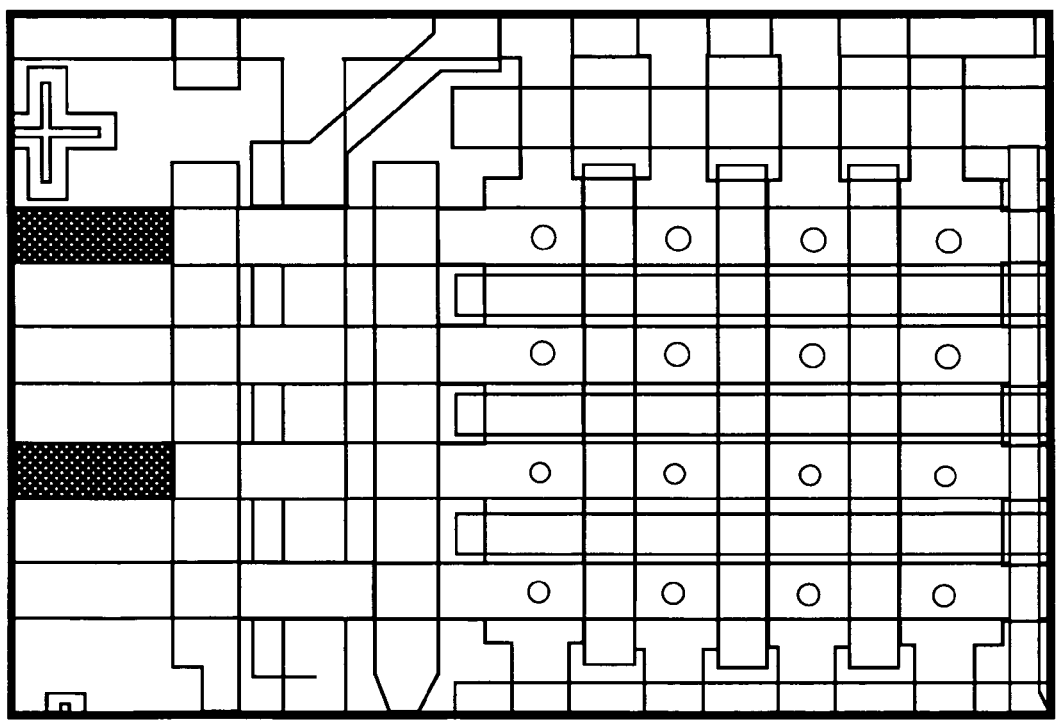
Figure 6F:
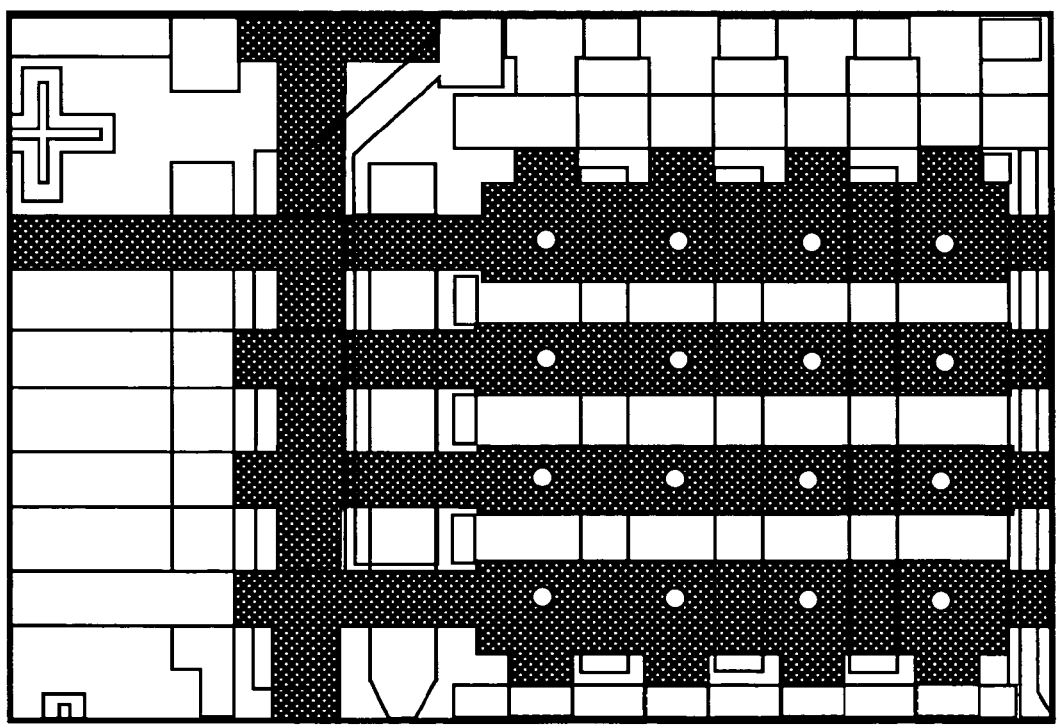
Figure 7:
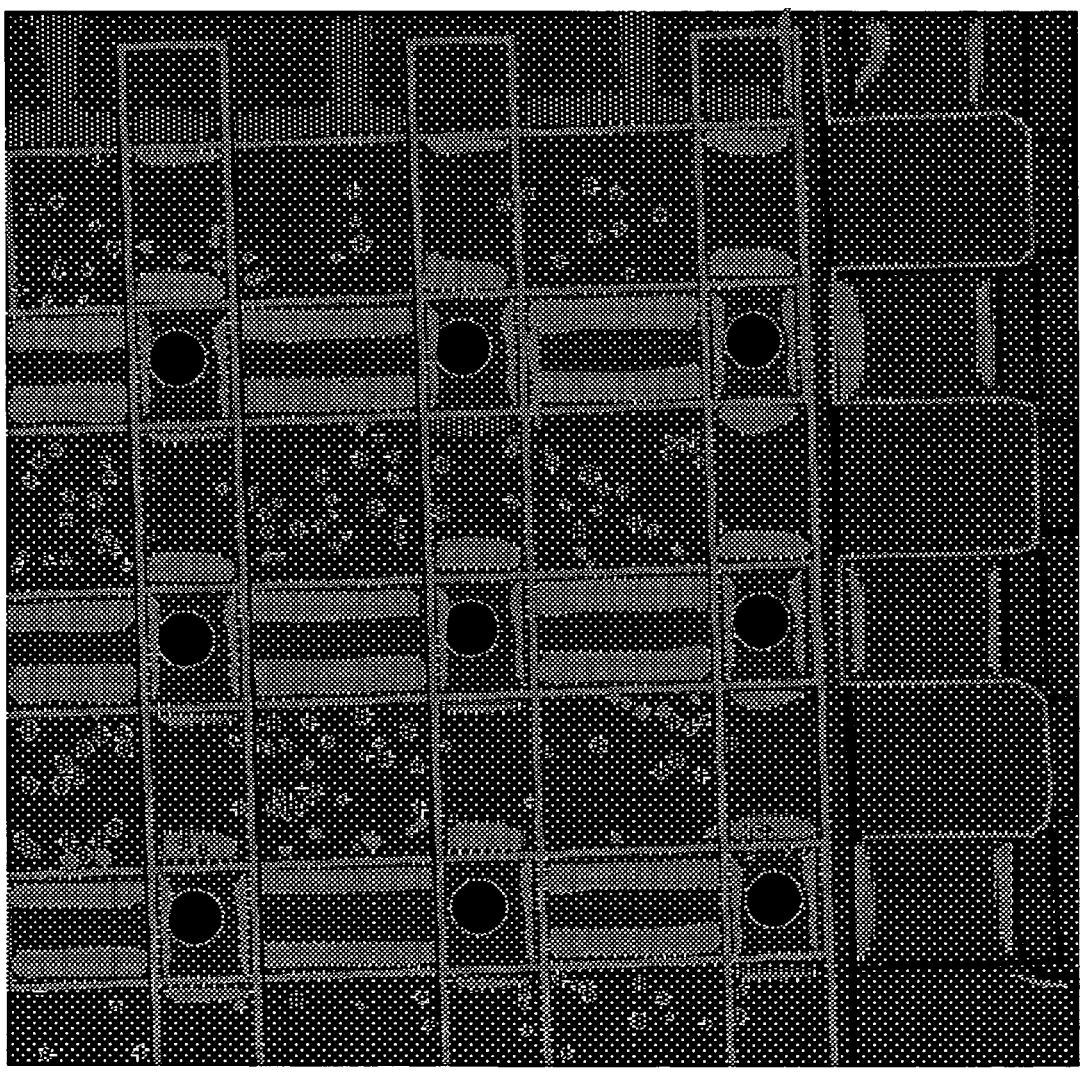
FIG. 7 shows HEK293 cells injected into a device of the design shown in FIGS. 5a-c.

FIGS. 6a-f demonstrate different flows achievable with the multiple reaction device. The design shown in FIG. 5 is capable of routing flows in the same way. FIG. 6a shows the 16 reaction chambers (wells) in the central reaction area, with circular pillars at their centers, can be connected columnwise to the column inlet channels and flushed vertically as shown here with dye. FIG. 6b shows the reaction wells can be connected rowwise to the row inlet channels and flushed horizontally. FIG. 6c shows both sets of barrier valves closed; the channels are isolated from each other, as indicated by the strips of white that now separate the chambers filled with dye. FIG. 6d shows the entire device can be flushed with fluid from a manifold inlet located to the upper left, or alternatively, FIG. 6e shows the entire device can be flushed with fluid from another manifold inlet. FIG. 6f shows that the flush can occur either vertically or horizontally.

FIG. 7 shows HEK293 cells injected into a device. The central cell reaction area was treated with BSA and fibronectin as detailed herein. HEK293 cells were trypsinized and washed off the bottom of a T75 cell culture flask, washed, resuspended, and injected as described. Excess cells were flushed away after 20 minutes at 37 degrees Celsius. Note that most of the barrier valve areas have been cleared of cells.

OTHER APPLICATIONS

As stated above, the stagnant cross channel array should be useful for experimenting on many eukaryotic cell types which can be bound to surfaces; bead suspensions can also be handled and deposited in a similar way. Possible experiments with cells which can be performed in this type of platform include: simple ligand screens and dose response curves; sequential ligand addition experiments probing correlations of cellular responses to different ligands, i.e. experiments to see how much the cell-specific variations in ligand responses are dependent on the cell state rather than the particular ligand in question; experiments which simultaneously probe several different cell types. In the second case, a shortened or absent recovery phase between ligand applications should also yield information on a cell's adaptation to external stimuli. In the last case, the device can be seeded twice with different types of cells, with a picture taken between seedings to allow identification of a cell's provenance during data analysis.

Most of these experiments may also be possible in the combinatorial design, albeit with a smaller subset of cells. In addition, this design may also be used to perform combinatorial chemical experiments, with some modifications to the barrier valves to allow reagent flushes in some, but not all, columns or rows. Additional applications include providing biological molecules to the reaction area or small molecules. Biological molecules such as DNA along with enzymatic reagents and buffers can be provided to a microfluidic device of the present disclosure.

In summary, the regulation of fluid flow by equalization of pressures in flow channels provides for a new method and device for providing cells to a microfluidic device.

While illustrative embodiments have been shown and described in the above description, numerous variations and alternative embodiments will occur to those skilled in the art. Such variations and alternative embodiments are contemplated, and can be made without departing from the scope of the invention as defined in the appended claims.

The invention claimed is:

1. A method for loading cells into a microfluidic device, comprising:
   a) providing a microfluidic device comprising:
      i) an inlet manifold that branches into at least two channels, said two channels comprising a first channel extending from the manifold to a first distal end and a second channel extending from the manifold to a second distal end ii) a plurality of cross-channels, each fluidically connected to the first channel at a first junction between the manifold and first distal end and fluidically connected to the second channel at a second junction between the manifold and second distal end, iii) a first valve in the first channel, positioned between the manifold and the first junction that is closest to the manifold, iv) a second valve in the second channel positioned between the second distal end and a second junction, b) with the first and second valves closed, introducing a cell suspension through the inlet manifold into the second channel, said cross-channels, and the first channel, and c) opening the first and second valves, thereby equalizing the pressure at the first and second junctions of the cross-channels so that cells in the cross-channels are protected from later fluid flushes without the cross-channels being valved off.

2. The method of claim 1, further comprising introducing a fluid through the inlet manifold while said first and second valves are open, thereby flushing the first and second channels but the not the cross-channels with the fluid.

3. The method of claim 2, wherein after flushing, the cells adhere to surfaces of the cross-channels.

4. The method of claim 1 wherein the distal ends of the first and second channels are in fluidic communication with each other through a second manifold.

5. The method of claim 2, wherein the fluid is a cell-free medium.

6. The method of claim 1, wherein the cross channels are heated to 37° C. and cells from the cell suspension are allowed to adhere to the surface of said cross-channels.

7. The method of claim 1, wherein the inlet manifold branches into two channels.

8. The method of claim 1, further comprising treating cells loaded into each of the flow channels with a different treatment.

9. The method of claim 1, further comprising staining the cells.

10. The method of claim 1, wherein the device further comprises a valve positioned on the inlet manifold before it branches into said channels.

11. The method of claim 1, wherein the cells are introduced through the manifold in step (b) under pneumatic pressure.

12. The method of claim 9, wherein the pneumatic pressure is about 0.3 psi.

13. A method for loading cells into a microfluidic device, comprising:

a) providing a microfluidic device comprising:

i) a flow channel connected to a cell source and a source of cell-free media;

ii) an exhaust channel;

iii) a plurality of cross-channels connected from the flow channel to the exhaust channel, the plurality comprising a first channel proximate to the cell source and a last cross channel distal from the cell source, wherein the cross-channels are configured for culturing cells;

iv) a first bypass channel connecting the flow channel to the exhaust channel, positioned between the cell source and the first cross channel;

v) a first valve positioned to control flow through the first bypass channel;

vi) a second bypass channel connecting the flow channel to the exhaust channel positioned distal from the last cross channel; and vii) a second valve positioned to control flow through the second bypass channel;

b) with the first and second valve closed, flowing a cell suspension through the flow channel and through the cross channels into the exhaust channel; then c) opening the first and second valves, thereby equalizing pressure between the flow channel, the cross-channels, and the exhaust channel; and then d) flowing a cell-free fluid through the flow channel and through the first and second bypass channels into the exhaust channel, thereby flushing cells from the flow channel and the exhaust channel, but not from the cross channels.

14. The method of claim 13, wherein the cross-channels of the device are adapted for cell adherence.

15. The method of claim 14 wherein the cross-channels are adapted by coating with fibronectin.

16. The method of claim 13, wherein the cell suspension is flowed through said cross channels in step (b) under pneumatic pressure.

* * * * *

UNITED STATES PATENT AND TRADEMARK OFFICE
CERTIFICATE OF CORRECTION

| | | |
|---|---|---|
| PATENT NO. | : 8,206,975 B2 | Page 1 of 1 |
| APPLICATION NO. | : 11/588852 | |
| DATED | : June 26, 2012 | |
| INVENTOR(S) | : Xiaoyan Robert Bao, Stephen R. Quake and Melvin I. Simon | |

It is certified that error appears in the above-identified patent and that said Letters Patent is hereby corrected as shown below:

In the Statement of Government Support Section,

Page 23, Col. 1, line 14, please delete
"The invention described herein was made in the performance of work under a grant from the National Institute of Health (NIH), Grant No. R01 HG002644. The U.S. government may have certain rights in the invention."
and insert
-- This invention was made with government support under Grant No. NS048499 awarded by the National Institutes of Health. The government has certain rights in the invention. --

Signed and Sealed this
Twenty-eighth Day of August, 2012

David J. Kappos
*Director of the United States Patent and Trademark Office*